United States Patent [19]

Inbasekaran et al.

[11] Patent Number: 5,386,002
[45] Date of Patent: Jan. 31, 1995

[54] FLUORENE BASED BISIMIDES AND THERMOPLASTIC POLYMERS THEREOF

[75] Inventors: Muthiah N. Inbasekaran; Daniel J. Murray; Michael N. Mang; James L. Brewbaker, all of Midland, Mich.

[73] Assignee: The Dow Chemical Company, Midland, Mich.

[21] Appl. No.: 161,969

[22] Filed: Dec. 3, 1993

[51] Int. Cl.[6] .............................................. C08G 73/10
[52] U.S. Cl. ...................................... 528/170; 528/125; 528/128; 528/171; 528/173; 528/174; 528/176; 528/185; 528/190; 528/191; 528/208; 528/288; 528/289; 528/322
[58] Field of Search ............... 528/185, 174, 172, 170, 528/171, 190, 191, 208, 288, 289, 322, 176, 125, 128

[56] References Cited

U.S. PATENT DOCUMENTS

| | | | |
|---|---|---|---|
| Re. 29,316 | 7/1977 | Bargain et al. | 528/170 |
| 3,380,964 | 4/1968 | Grundschober et al. | 526/209 |
| 3,730,946 | 5/1973 | Heath et al. | 528/185 |
| 3,968,083 | 7/1976 | Quinn | 528/208 |
| 4,005,134 | 1/1977 | Markezich | 562/473 |
| 4,297,474 | 10/1981 | Williams et al. | 528/170 |
| 4,499,165 | 2/1985 | Molaire | 430/17 |
| 4,584,258 | 4/1986 | Detty et al. | 430/270 |
| 4,732,963 | 3/1988 | Wank | 528/205 |
| 5,082,920 | 1/1992 | Harper | 528/205 |
| 5,104,960 | 4/1992 | Inbasekaran et al. | 528/125 |
| 5,171,820 | 12/1992 | Mang et al. | 528/87 |

OTHER PUBLICATIONS

Chin-Ping Yang, "Preparation and properties of cardo poly(amide-imide)s derived from 9,9-bis(4-aminophenyl)fluorene, trimellitic anhydride, and various aromatic diamines," *Makromol Chem*, vol. 193, pp. 445–453 Oct. (1992).
J. K. Stille, "Polyquinolines Containing Fluorene and Anthrone Cardo Units: Synthesis and Properties," *Macromolecules*, vol. 14, pp. 486–493 May/Jun., (1981).
K. L. Mittal, "Polyetherimide: A Versatile, Processable Thermoplastic," *Polyimides*, vol. 1, Plenum Press, New York and London, pp. 149–161 (1984).
R. W. Lenz, *Organic Chemistry of Synthetic High Polymers*, John Wiley & Sons, pp. 82–95, (1967).
V. V. Rode et al., "Effect of Amide Bonds on the Thermal Stability of Polyimides," *Vysokomolekulyarnye Soedineniya*, Ser. A, 12(7), 1566–1573 Oct. 19, (1970).

*Primary Examiner*—Morton Foelak
*Assistant Examiner*—P. Hampton-Hightower
*Attorney, Agent, or Firm*—Robert M. O'Keefe

[57] ABSTRACT

Polyetherimides, polyesterimides, poly(ester etherimides) and poly(carbonate imides) which are thermoplastic, polymeric materials contain divalent bisimides of formula

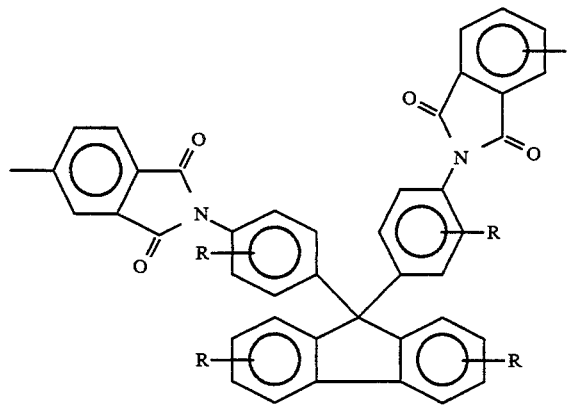

wherein R is independently in each occurrence hydrogen, alkyl of from 1 to 20 carbons, aryl or aralkyl of from 1 to 20 carbons, halogen or $NO_2$. Novel monomeric bisimides corresponding to the above formula are also disclosed.

28 Claims, No Drawings

FLUORENE BASED BISIMIDES AND THERMOPLASTIC POLYMERS THEREOF

BACKGROUND OF INVENTION

This invention relates to bisimides and polymers made from bisimides.

Bisimides and polyetherimides derived therefrom are known. For example, Serfaty reports in *Polyimides: Synthesis, Characterization, and Applications*, Volume 1 (1984) at page 149 that polyetherimide was a resin introduced commercially in 1982. This polyetherimide was made from bis{1,3-(4-nitrophthalimido)} benzene and bisphenol A. This polyetherimide is a thermoplastic which has been used in electrical, electronics, transportation, and appliance applications. More recently, Yang et al. reported in *Makromol. Chem.*, volume 193, pages 445–453 (1992), the preparation of cardo poly(amide-imide)s derived from 9,9-bis(4-aminophenyl)fluorene, trimellitic anhydride, and various aromatic diamines. However, this disclosure is limited to a specific fluorene derivative and to specific polyamides derived therefrom. Current research efforts have been directed at finding new aromatic bisimides and polymers made therefrom.

SUMMARY OF INVENTION

This invention, in a first respect, is a thermoplastic, polymeric material containing a repeating unit corresponding to Formula I:

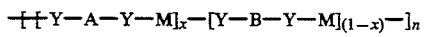

wherein A is a bisimide of Formula IIA:

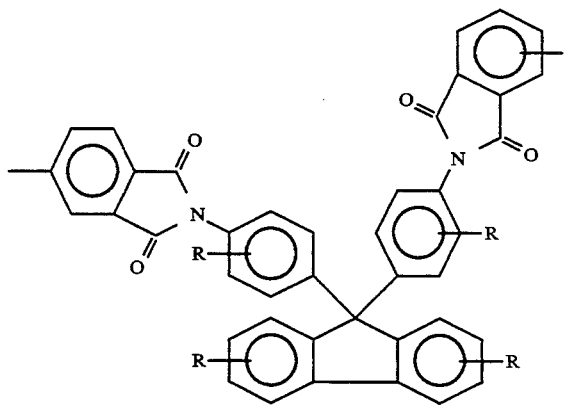

wherein R is independently in each occurrence hydrogen, alkyl of from 1 to 20 carbons, aryl or aralkyl of from 1 to 20 carbons, halogen, or $NO_2$; x is from about 0.1 to 1; n is from about 5 to about 1000; Y is independently in each occurrence a covalent bond or CO; B is independently in each occurrence a divalent hydrocarbylene moiety optionally substituted with halogen, alkyl, aryl, aralkyl, wherein the entire divalent hydrocarbylene moiety contains from 1 to 50 carbons; or wherein B is a divalent moiety of Formula III:

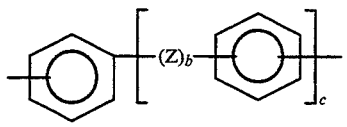

wherein Z is $CH_2$, $CH_2CH_2$, $C(CH_3)_2$, $CF_2$, $C(CF_3)_2$, $OCH_2O$, $OCH_2CH_2O$, $CO_3$, O, S, SO, $SO_2$, $SO_3$; b is 0 or 1; and c is 0, 1, or 2; wherein M is independently in each occurrence —O—B—O—, —O—$CH_2$CHOH$CH_2$—O—B—O—$CH_2$CHOH$CH_2$—O—, —O—$CH_2$CHOH$CH_2$—O—, —O—CO—O—, or —O—CO—B—CO—O— with the proviso that M is not —O—CO—O— or —O—CO—B—CO—O— when Y is —CO—.

In a second respect, this invention is a bisimide of Formula II:

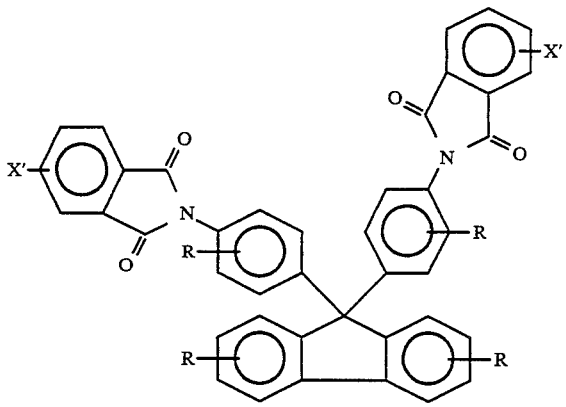

wherein R is independently hydrogen, alkyl of from 1 to 20 carbons, aryl or aralkyl of from 1 to 20 carbons, halogen, or $NO_2$; X' is F, Cl, OH, or $NO_2$.

DETAILED DESCRIPTION OF THE INVENTION

The aromatic bisimides used as monomers in the practice of this invention to prepare the materials of Formula I are of Formula IIB:

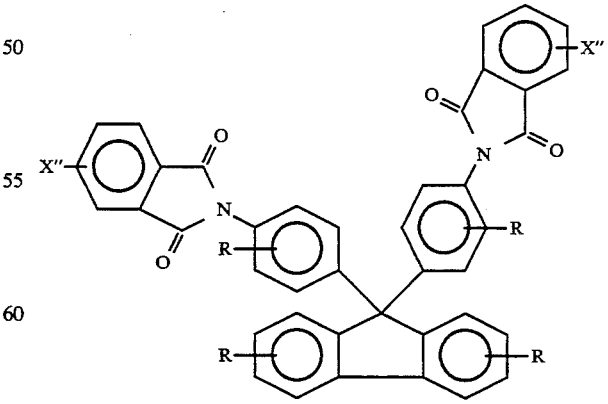

wherein R is as described hereinabove; XΔ is F, Cl, OH, $NO_2$, COOH, COCl, or $COOR^2$ wherein $R^2$ is an alkyl or aryl group of from 1 to 20 carbons. Preferably, X" is F when the bisimide is used to make polyetherimides;

X" is COOH or COCl when the bisimide is used to make polyesterimides and poly(ester ether)imides; and X" is OH when the bisimide is used to make polycarbonates-imides.

For each of Formulas II, IIA, IIB, when R is alkyl, the alkyl group can be linear, branched, or cyclic. Exemplary of aryl or aralkyl R groups include phenyl, biphenyl, naphthyl, benzyl, methylphenyl. R is preferably independently in each occurrence hydrogen or alkyl of from 1 to 6 carbons; most preferably, R is hydrogen in each occurrence for each of Formulas II, IIA, IIB.

The novel aromatic bisimides of Formula II are useful as monomers as described herein. In Formula II, X' is preferably F or OH.

In Formula I, a polyetherimide is a material wherein Y is a covalent bond and M is —O—B—O—. A polyesterimide is a material wherein Y is CO and M is —O—B—O—. A polycarbonate-imide is a material wherein M is —O—CO—O— or —O—CO—B—CO—O— and Y is a covalent bond. A poly(ester ether)imide is a material wherein Y is CO and M is —O—CH$_2$CHOHCH$_2$—O—B—O—CH$_2$CHOHCH$_2$—O— or —O—CH$_2$CHOHCH$_2$—O— Units of Formula I correspond to the residue of monomeric aromatic bisimides of Formula IIB. In Formula I, x is preferably in the range of 0.25 to 0.75.

The preferred divalent hydrocarbylene moieties of B in Formula I include divalent aromatic moieties such as arylene, alkylenearylene, dialkylenearylene, diaryleneketone, diarylenesulfone, diarylenesulfoxide, alkylidene-diarylene, diarylene oxide, diarylene sulfide, diarlyenecyanomethane or divalent aliphatic moieties such as alkylene, alkylene oxide, alkylene sulfide, alkylene sulfoxide, or the like. More preferred divalent moieties include 1,3-phenylene, 1,4-phenylene, biphenylene, napthylene, isopropylidenediphenylene, methylenediphenylene, oxydiphenylene, diphenylene sulfide and diphenylene sulfoxide. More preferred moieties include 1,3-phenylene, 1,4-phenylene, biphenylene, napthylene and isopropylidenediphenylene. In Formula III, Z is preferably CH$_2$, CH$_2$CH$_2$, C(CH$_3$)$_2$, CF$_2$, C(CF$_3$)$_2$, OCH$_2$CH$_2$O or O; more preferably Z is O.

The aromatic bisimides are prepared generally by condensing 9,9-bis(4-aminophenyl)fluorene substituted such that a final aromatic bisimide of Formula II or IIB is provided with a phthalic anhydride substituted by X' or X" in accordance with Formula II or IIB. The substituted 9,9-bis(4-aminophenyl)fluorene compound can be prepared according to the procedure of Stille et al., *Macromolecules*, volume 14, 486 (1981). The phthalic anhydrides useful in the practice of this invention are readily made by well known methods and are readily available commercially. The general reaction conditions for the condensation of the substituted 9,9-bis(4-aminophenyl)fluorene and the phthalic anhydride are as follows. From about 2 to about 4 equivalents, preferably from about 2 to about 2.6 equivalents, and most preferably from about 2.1 to about 2.2 equivalents of the phthalic anhydride and one equivalent of the unsubstituted or substituted 9,9-bis(4-aminophenyl)fluorene are combined in a dipolar aprotic solvent such as dimethylformamide (DMF), dimethylsulfoxide (DMSO), N-methylpyrrolidine (NMP), acetic acid and m-cresol. The condensation reaction is run at a temperature typically greater than or equal to about 20° C., preferably greater than or equal to about 50° C., more preferably greater than or equal to about 120° C.; typically less than or equal to about 200° C., preferably less than or equal to about 170° C. and more preferably less than or equal to about 160° C. Pressure can be atmospheric, superatmospheric or subatmospheric. The condensation reaction is carried out for from about 10 minutes to about 100 hours, depending on the amount of reactants, temperature, solvent, pressure and the like. The aromatic bisimides produced from the condensation reaction are recovered using well known techniques such as filtration and distillation and likewise purified by well known techniques such as distillation, washing with an organic solvent, recrystallization and chromatography. It should be noted that an aromatic bisimide bis-acid chloride of Formula IIB wherein X" is COCl can be prepared readily by well known techniques from the aromatic bisimide bis-acid of Formula IIB wherein X" is COOH such as by reaction of the bis-acid with thionyl chloride. In the case where X' or X" is hydroxy, the bisimide can be prepared by reacting 2 to 3 molar equivalents of the 4-hydroxyphthalic acid with one molar equivalent of 9,9-bis(4-aminophenyl)fluorene in refluxing acetic acid.

The aromatic bisimides of this invention can be employed as a monomer in the production of various thermoplastic, polymeric materials. For instance, the aromatic bisimides can be used to produce polycarbonate imides, polyesterimides, poly(carbonate ester imides), polyetherimides and poly(ester ether)imides.

The techniques used to produce polyetherimides are well known in the art. See, for example, U.S. Pat. No. 4,297,474. Typically, in the practice of this invention, a substituted aromatic bisimide is reacted with an alkali metal phenate to form the polyetherimide. The alkali metal phenate can be either monocyclic or polycyclic and contain two phenate groups. The phenates are reacted to yield polymeric materials as described above containing an —O—B—O— group wherein this group is a phenate residue. Group B when of Formula III thus corresponds to materials derived from phenates. Suitable phenols from which the phenates can be derived are of Formula IIIA:

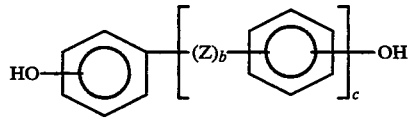

wherein Z, b and c are as described above. Examples of suitable phenols from which the phenates are derived include 2,2-bis(4-hydroxyphenyl) propane, 4,4'-dihydroxy diphenyl oxide, 4,4'-dihydroxydiphenyl sulfide, 4,4'-dihydroxydiphenyl sulfoxide, 1,1,1,3,3,3,-hexafluoro-2,2-bis(4-hydroxyphenyl)propane, 4,4'-dihydroxydiphen methane, 1,4-benzenediol, and 1,3-benzenediol. The alkali metal phenate can be added directly or formed by reaction of an alkali metal salt such as sodium or potassium bicarbonate with a phenol. In the polymerization of the alkali metal phenate with the substituted aromatic bisimide, a solvent can be used such as dimethyl-acetamide, dimethylformamide, N-methylpyrrolidone, and diglyme. After polymerization of the reactants, the polyetherimide is recovered and purified by well known methods. Alternatively, the polyetherimides can also be prepared by reacting the fluoro-substituted bisimide with the trimethylsilyl derivative of the bisphenol in the presence of a catalyst such as an alkali metal fluoride, preferably cesium fluoride, in an aprotic organic solvent such as diphenyl sulfone. See, in this regard, H. R. Kricheldorf et al., *J. of Polymer Science: Polymer Chemistry Ed.*, volume 21, pages 2283-2289, (1983).

The polyesterimides can be prepared readily by well known techniques. See, for example, S. C. Temin, "Polycarboxylic Esters," Chapter 12 in "Interfacial Synthesis," F. Millich and C. E. Carraher, Jr., editors, Marcel Dekker, New York, New York, 1977; S. R. Sandler, W. Karo, "Polymer Synthesis," Academic Press New York, New York, 1974, pages 55-72. Generally, the polyesterimides can be prepared by reacting a phenol of Formula III with an aromatic bisimide bisacid chloride of Formula I wherein X is COCl. More than one phenol can be employed if desired to form a polyesterimide containing two or more types of ester linkages. Similarly, an aromatic bis-acid chloride comonomer can be added to vary the properties of the resulting polyesterimide. Examples of a suitable aromatic bis-acid chloride comonomers include isophthaloyl chloride and terephthaloyl chloride. The reaction of the phenol with the aromatic bisimide bisacid chloride can be performed by agitating an weak aqueous sodium hydroxide solution which contains the phenol, with a mixture of the aromatic bisimide bisacid chloride in an organic solvent such as methylene chloride. The reaction is typically carried out in a Waring blender at from 5° C. to 25° C. for varying times depending on temperature, amount of reactants, amount of agitation and other process conditions.

The aromatic bisimides of this invention can also be employed in the production of various poly(ester ether)imides. The poly(ester ether)imides can be prepared readily by well known techniques. For example, see U.S. Pat. No. 5,171,820. Generally, the poly(ester ether)imides are prepared by reaction of an aromatic bisimide bis-acid of Formula I wherein X is COOH with an aromatic ether epoxide under conditions including the use of an onium catalyst sufficient to cause the acid moieties to react with epoxy moieties to form a polymer backbone having ester and ether linkages. The polyesters are prepared at temperatures in the range from about 60° C. to about 160° C. under an inert atmosphere.

Examples of preferred onium catalysts include tetrahydrocarbyl quaternary ammonium haldies wherein hydrocarbyl is a monovalent hydrocarbon radical such as alkyl, aryl, cycloalkyl, aralkyl and alkaryl, preferably having from 1 to 16 carbon atoms. Examples of such preferred onium catalysts include tetrakis(n-butyl)ammonium bromide and the corresponding chloride, iodide and fluoride, with tetrakis(n-butyl)ammonium bromide being most preferred. Other suitable onium catalysts include tetrahydrocarbyl phosphonium halides such as ethyl triphenylphosphonium iodide and tetraphenylphosphonium bromide.

The polymeric materials of this invention can be used to make films, coatings and as injection moldable plastics to make mold parts, for example. The polymeric materials of this invention can be reinforced with a variety of particulated fillers such as glass fibers, silica fillers and carbon whiskers. The particulated fillers can be added to the polymeric materials prior to polymer formulation by effecting polymerization in the presence of filler. Melt blending and solution blending can also be used to add the particulated fillers to the polymeric materials of this invention.

The polymers of the present invention are processible as thermoplastics. A thermoplastic is defined as a material which flows at temperatures above its glass transition temperature and in which crosslinking or network formation does not occur. Thermoplastic processing is defined as heating a material to a temperature sufficient for flow to occur, with subsequent or concurrent forming into a shaped article. The article can be reheated and reformed any desired number of times, and the polymer does not undergo crosslinking or network formation during this handling. A test for crosslinking can be made by attempting to dissolve the material in a solvent, especially after exposure to the temperatures encountered during thermoplastic processing. Crosslinked materials will not dissolve, while uncrosslinked materials will dissolve. Thermoplastics may be extruded at temperatures above their glass transition temperatures or they can be compression molded into films and plaques, and they remain both soluble and processible after such thermal treatment.

The following examples are given to illustrate the invention and should not be interpreted as limiting it in any way. Unless stated otherwise, all parts and percentages are given by weight.

EXAMPLE 1:

Preparation of Several Bisimides 9,9-Bis{4-(4-fluorophthal-imido)phenyl}fluorene A mixture of 9,9-bis(4-aminophenyl)fluorene (17.4 g, 50 mmol), 4-fluorophthalic anhydride (18.3 g, 110 mmol), and 250 ml of acetic acid was stirred and heated under reflux for five hours and then stirred at ambient temperature overnight. A colorless precipitate formed which was filtered, washed twice with 150 ml of ethanol, washed twice with 100 ml of hexane, suction-dried for two hours, and then dried in a vacuum oven at 120° C. for 16 hours. The title compound was isolated as a colorless powder (29.2 g, 90.6% yield) that had melting point of 323.5°-326° C. and a $^1$H NMR spectrum (DMSO-$d_6$) corresponding to $\delta 8.02$ (m, 4H), 7.86 (dd, 2H), 7.72 (m, 2H), 7.60 (d, 2H), 7.46 (t, 2H), and 7.35 (m, 10H).

9,9-Bis{4-(4-carboxy-phthalimido)phenyl}fluorene

To a stirred mixture of 9,9-bis(4-aminophenyl)fluorene (13.9 g, 40 mmol) and 80 ml of m-cresol was added 1,2,4-benzenetricarboxylic anhydride (16.1 g, 84 mmol) over two minutes. The resulting mixture was stirred under gentle reflux (163°-170° C.) for three hours and then at ambient temperature for 16 hours. A pale yellow precipitate was filtered, washed with methanol, washed with toluene, and then dried in a vacuum oven at 100°-105° C. for 16 hours to provide the title compound as a pale yellow powder (24.7 g, 88.7% yield) that had a melting point of 328°-331° C. and a $^1$H NMR spectrum (DMSO $d_6$) corresponding to $\delta 8.39$ (d,2H), 8.29 (br s, 2H), 8.05 (d, 2H), 8.00 (d, 2H), 7.61 (d, 2H), and 7.40 (m, 12H).

Bis-Acid Chloride of 9,9-Bis{4-(4-carboxyphthalimido)-phenyl}fluorene

The bis-acid chloride was prepared by stirring and heating a mixture of the acid (12 g), as prepared above, 50 ml of thionyl chloride, and a few drops of DMF (dimethylformamide) under reflux for four hours. Next, the excess thionyl chloride was evaporated off and the residue was triturated with 200 ml of ether. The bis-acid chloride was isolated as a tan powder (11.9 g, 94.1% yield) having a melting point of 301°–304° C.

9,9-Bis{4-(4-hydroxy-phthalimido)phenyl}fluorene

A mixture of 4-hydroxyphthalic acid (4.0 g, 22 mmol), 9,9-bis(4-aminophenyl)fluorene (3.5 g, 10 mmol), and 40 ml of acetic acid was stirred and heated under reflux for 48 hours. After cooling to room temperature, the precipitate was collected by filtration and washed with acetic acid (2×25 ml) to provide the title compound as a colorless powder having a melting point greater than 300° C. (3.4 g, 53.1% yield). The nuclear magnetic resonance and infrared spectrum were consistent with the structure.

9,9-Bis{4-(4-nitrophthalimido)phenyl}fluorene

A mixture of 9,9-bis(4-aminophenyl)fluorene (3.5 g, 10 mmol) and 40 ml of acetic acid was stirred and then 4-nitrophthalic anhydride (4.1 g, 21 mmol) was added to the mixture. The resulting mixture was stirred and heated under reflux for 7 hours. After cooling, the beige-colored precipitate was filtered, washed with acetic acid (2×100 ml) and then with water (500 ml). The washed precipitate was recrystallized from dimethyl-fromamide-methanol to provide the title compound as an off-white powder (5.1 g, 73% yield) having a melting point of 360°–363° C.

EXAMPLE 2:

Preparation of a Polyesterimide from the Bis-Acid Chloride of 9,9-Bis{4-(4-carboxyphthalimido)phenyl}fluorene, Isophthaloyl Chloride, and Bisphenol A A solution of bisphenol A (0,457 g, 2.00 mmol), tetrabutylammonium bromide (0,013 g, 0.04 mmol) in 44 ml of 0.1N aqueous sodium hydroxide and a solution of the bis-acid chloride (0,734 g, 1.00 mmol) and isophthaloyl chloride (0,203 g, (1.00 mmol) in 300 ml of methylene chloride were stirred in a water cooled Waring blender at about 10° C. for 20 minutes. Saturated sodium chloride solution (100 ml) was added to the Waring blender to break the resulting emulsion. The organic phase that separated was washed with 100 ml portions of 1N HCl, 5% NaHCO$_3$, and water and then was dried over MgSO$_4$. The polymer solution was reduced in volume to 100 ml and the polymer was precipitated by slowly adding the solution to 300 ml of hexane in a Waring blender. The off-white solid (0.89 g, 70% yield) was isolated by filtration and dried in a vacuum oven at 100° C. for one hour. The ratio of the units of the bisimide, isophthaloyl, and bisphenol A components was found to be 1.02/1.00/1.02 by $^1$H NMR spectroscopy. The inherent viscosity of the polymer was taken at 25° C. in methylene chloride at a concentration of 0.5 g/dL and found to be 0.25 dL/g. The Tg of the polymer was determined by DSC at a scan rate of 10° C. was 277° C.

EXAMPLE 3:

Preparation of a Poly(ester ether) imide 9,9-Bis{4-(4-carboxyphthalimido)phenyl}-fluorene and Bisphenol A Diglycidyl Ether To a 100 ml minireactor equipped with a mechanical stirrer, nitrogen inlet, and thermocouple was added bisphenol A diglycidyl ether (4.96 g, 14.5 mmol), 9,9-bis{4-(4-carboxyphthalimido)phenyl}fluorene (10.1 g, 14.5 mmol), and tetra-n-butylammonium bromide (4.00 g). Next, diglyme (35 ml) was added under a flow of nitrogen and the resulting mixture was heated to 110° C. under nitrogen for one and one-half hours. Then, glacial acetic acid (3 ml) was added and heating was continued at 110° C. for two hours. DMF (35 ml) was added to dilute the mixture, and the diluted mixture was allowed to cool to room temperature. The polymer was isolated by pouring the solution into water (500 ml) in a Waring blender. The poly(ester ether) was collected by filtration, then dissolved in DMF (100 ml) and reprecipitated into water as described above. The poly(ester ether)imide was collected by suction filtration and was dried overnight in a vacuum oven at 80° C. The dried poly(ester ether)imide (12.4 g, 83% yield) had an inherent viscosity of 0.39 dL/g, as measured in dimethylformamide at 25° C. at a concentration of 0.5 g/dL. The poly(ester ether) had a Tg of 146° C. and a $^1$H NMR spectrum (DMSO d$_6$) corresponding to δ8.41 (m, 4H), 8.10–7.95 (m, 4H), 7.60 (d, 2H), 7.43–7.33 (m, 12H), 7.09 (d, 4H), 6.85 (d, 4H), 5.62 (br s, 1.5H), 5.37 (br s, 0.5H), 5.22 (br s, 0.5H), 4.45–4.04 (m, 9.5H), and 1.56 (s, 6H).

EXAMPLE 4:

Preparation of a Polyetherimide from 9,9-Bis(4-(fluorophthalimido)phenyl)fluorene and Bisphenol A A 250 ml flask was charged with 9,9-bis(4-(fluorophthalimido)phenyl)fluorene (19.34 g, 30 mmol), bisphenol A (6.85 g, 30 mmol), potassium 5 carbonate (18.65 g, 135 mmol), 90 ml of dimethylacetamide, and 60 ml of toluene. The mixture was stirred under a continuous nitrogen purge and heated to 100° C. for 30 minutes and then to 135° C. for 90 hours. The viscous solution was poured into 2 liters of methanol and the resulting solid was then slurried with 200 ml of methylene chloride, then with water. The off white solid was filtered and dried in a vacuum oven at 150° C. for 16 hours. T$_g$ was not detectable by Differential Scanning Calorimetry. The solid had an inherent viscosity of 0.54 dL/g measured in dimethylacetamide at 25° C. at a concentration of 0.5 g/dL. The $^1$H and $^{13}$C NMR spectra (D$_6$DMSO) were consistent with the assigned structure.

EXAMPLE 5:

Preparation of a Polyetherimide from 9,9-Bis(4-(fluorophthalimido)phenyl)fluorene and Trimethylsilylated Bisphenol A A 300 ml resin kettle was charged with 9,9-bis(4-fluorophthalimido)phenyl)fluorene (19.34 g, 30 mmol), 2,2-bis(4,4'-trimethylsiloxyphenyl)propane (10.90 g, 29 mmol), diphenyl sulfone (10 g), and chlorobenzene (25 ml). The mixture was stirred under a continuous nitrogen purge and heated to 335° C. After the chlorobenzene distillate was collected, approximately 2 mg of cesium fluoride was added to the resin kettle. Immediately after addition of the cesium fluoride catalyst, a liquid rapidly distilled from the solution. The reaction was stirred for 20 minutes and the reactor was removed from the heating bath. The polymer was then slurried with 200 ml of dimethylacetamide. The dimethylacetamide soluble portion was precipitated into 2 liters of methanol and the resulting solid dried in a vacuum oven at 150° C. for 16 hours. T$_g$ was 262° C. at 10° C./minute. The dry solid weighed 23.1 g (92.5% yield). A compression molded film of the dry polymer of 20 mils thickness molded at 330° C. was brittle. The inherent viscosity of the polymer was 0.22 dL/g measured in dimethylacetamide at 25° C. at a concentration of 0.5 g/dL.

What is claimed is:

1. A thermoplastic, polymeric material containing a repeating unit corresponding to Formula I:

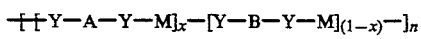

wherein A is a bisimide of Formula IIA:

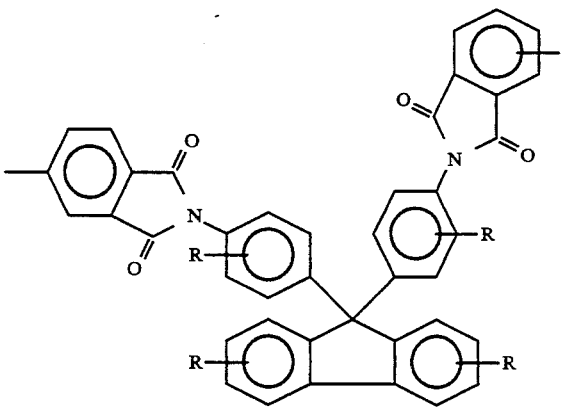

wherein R is independently in each occurrence hydrogen, alkyl of from 1 to 20 carbons, aryl or aralkyl of from 1 to 20 carbons, halogen, or $NO_2$;

x is from about 0.1 to 1;

n is from about 5 to about 1000;

Y is independently in each occurrence a covalent bond or CO;

B is independently in each occurrence a divalent hydrocarbylene moiety optionally substituted with halogen, alkyl, aryl, aralkyl, wherein the entire divalent hydrocarbylene moiety contains from 1 to 50 carbons; or wherein B is a divalent moiety of Formula III:

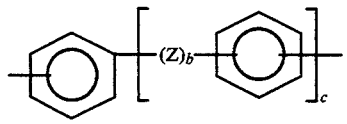

wherein Z is $CH_2$, $CH_2CH_2$, $C(CH_3)_2$, $CF_2$, $C(CF_3)_2$, $OCH_2O$, $OCH_2CH_2O$, $CO_3$, O, S, SO, $SO_2$, $SO_3$; b is 0 or 1; and c is 0, 1, or 2;

wherein M is independently in each occurrence —O—B—O—, —O—$CH_2$CHOH$CH_2$—O—B—O—$CH_2$-CHOH$CH_2$—O—, —O—$CH_2$CHOH$CH_2$—O—, —O—CO—O—, or —O—CO—B—CO—O— with the proviso that M is not —O—CO—O— or —O—CO—B—CO—O— when Y is —CO—.

2. The thermoplastic, polymeric material of claim 1 wherein R is independently in each occurrence hydrogen or alkyl of 1 to 6 carbons.

3. The thermoplastic, polymeric material of claim 1 wherein R is hydrogen in each occurrence.

4. The thermoplastic, polymeric material of claim 1 wherein x is in the range from 0.25 to 0.75.

5. The thermoplastic, polymeric material of claim 1 wherein the material is a polyetherimide, Y is a covalent bond and M is —O—B—O—.

6. The thermoplastic, polymeric material of claim 5 wherein R is independently in each occurrence hydrogen or alkyl of 1 to 6 carbons.

7. The thermoplastic, polymeric material of claim 5 wherein R is hydrogen in each occurrence.

8. The thermoplastic, polymeric material of claim 5 wherein x is in the range from 0.25 to 0.75.

9. The thermoplastic, polymeric material of claim 5 wherein B is 1,3-phenylene, 1,4-phenylene, biphenylene, napthylene, isopropylidenediphenylene, methylenediphenylene, oxydiphenylene, diphenylene sulfide, or diphenylene sulfoxide.

10. The thermoplastic, polymeric material of claim 1 wherein the material is a polyetherimide and Y is a covalent bond, R is hydrogen in each occurrence, x is in the range from 0.25 to 0.75, B is 1,3-phenylene, 1,4-phenylene, biphenylene, napthylene, isopropylidenediphenylene, methylenediphenylene, oxydiphenylene, diphenylene sulfide, or diphenylene sulfoxide and M is —O—B—O—.

11. The thermoplastic, polymeric material of claim 1 wherein the material is a polyesterimide, Y is CO and M is —O—B—O—.

12. The thermoplastic, polymeric material of claim 11 wherein R is independently in each occurrence hydrogen or alkyl of 1 to 6 carbons.

13. The thermoplastic, polymeric material of claim 11 wherein R is hydrogen in each occurrence.

14. The thermoplastic, polymeric material of claim 11 wherein x is in the range from 0.25 to 0.75.

15. The thermoplastic, polymeric material of claim 11 wherein B is 1,3-phenylene, 1,4-phenylene, biphenylene, napthylene, isopropylidenediphenylene, methylenediphenylene, oxydiphenylene, diphenylene sulfide, diphenylene sulfoxide, ethylene, propylene, or butylene.

16. The thermoplastic, polymeric material of claim 1 wherein the material is a polyesterimide, Y is CO, M is —O—B—O—, R is hydrogen in each occurrence, x is in the range from 0.25 to 0.75 and B is 1,3-phenylene, 1,4-phenylene, biphenylene, napthylene, isopropylidenediphenylene, methylenediphenylene, oxydiphenylene, diphenylene sulfide, diphenylene sulfoxide, ethylene, propylene, or butylene.

17. The thermoplastic, polymeric material of claim 1 wherein the material is a polycarbonate-imide, M is —O—CO—O— or —O—CO—B—CO—O— and Y is a covalent bond.

18. The thermoplastic, polymeric material of claim 17 wherein R is independently in each occurrence hydrogen or alkyl of 1 to 6 carbons.

19. The thermoplastic, polymeric material of claim 17 wherein R is hydrogen in each occurrence.

20. The thermoplastic, polymeric material of claim 17 wherein x is in the range from 0.25 to 0.75.

21. The thermoplastic, polymeric material of claim 17 wherein B is 1,3-phenylene, 1,4-phenylene, biphenylene, napthylene, isopropylidenediphenylene, methylenediphenylene, oxydiphenylene, diphenylene sulfide, or diphenylene sulfoxide.

22. The thermoplastic, polymeric material of claim 1 wherein the material is a polycarbonate-imide, M is —O—CO—O— or —O—CO—B—CO—O—, Y is a covalent bond, R is hydrogen in each occurrence, x is in the range from 0.25 to 0.75, and B is 1,3-phenylene, 1,4-phenylene, biphenylene, napthylene, isopropylidenediphenylene, methylenediphenylene, oxydiphenylene, diphenylene sulfide, or diphenylene sulfoxide.

23. The thermoplastic, polymeric material of claim 1 wherein the material is a poly(ester ether)imide, Y is CO and M is —O—CH$_2$CHOHCH$_2$—O—B—O—CH$_2$CHOHCH$_2$—O— or —O—CH$_2$CHOHCH$_2$—O—.

24. The thermoplastic, polymeric material of claim 23 wherein R is independently in each occurrence hydrogen or alkyl of 1 to 6 carbons.

25. The thermoplastic, polymeric material of claim 23 wherein R is hydrogen in each occurrence.

26. The thermoplastic, polymeric material of claim 23 wherein x is in the range from 0.25 to 0.75.

27. The thermoplastic, polymeric material of claim 23 wherein B is 1,3-phenylene, 1,4-phenylene, biphenylene, napthylene, isopropylidenediphenylene, methylenediphenylene, oxydiphenylene, diphenylene sulfide, or diphenylene sulfoxide.

28. The thermoplastic, polymeric material of claim 1 wherein the material is a poly(ester ether)imide, Y is CO, M is —O—CH$_2$CHOHCH$_2$—O—B—O—CH$_2$CHOHCH$_2$—O— or —O—CH$_2$CHOHCH$_2$—O—, R is hydrogen in each occurrence, x is in the range from 0.25 to 0.75 and B is 1,3-phenylene, 1,4-phenylene, biphenylene, napthylene, isopropylidenediphenylene, methylenediphenylene, oxydiphenylene, diphenylene sulfide, or diphenylene sulfoxide.

* * * * *